United States Patent [19]

Kaufman

[11] 4,126,527
[45] Nov. 21, 1978

[54] RADIATION CURABLE COATINGS CONTAINING HYDROXY FUNCTIONAL POLYETHERS AND POLYESTERS OF MONOETHYLENIC ACIDS OR HYDROXY ESTERS THEREOF

[75] Inventor: Marvin L. Kaufman, Bridgewater, N.J.

[73] Assignee: Mobil Oil Corporation, New York, N.Y.

[21] Appl. No.: 856,692

[22] Filed: Dec. 2, 1977

Related U.S. Application Data

[63] Continuation-in-part of Ser. No. 618,101, Sep. 30, 1975, abandoned.

[51] Int. Cl.$^2$ ............................................. C08F 2/46
[52] U.S. Cl. ........................... 204/159.22; 204/159.16; 204/159.23
[58] Field of Search ............................... 260/78.3 UA; 204/159.22, 159.23, 159.16, 159.14

[56] References Cited

U.S. PATENT DOCUMENTS

| | | | |
|---|---|---|---|
| 2,945,012 | 7/1960 | Berens | 260/78.3 UA |
| 3,453,345 | 7/1969 | Malrey et al. | 260/834 |
| 3,485,732 | 12/1969 | D'Alelio | 204/159.22 |
| 3,485,733 | 12/1969 | D'Alelio | 204/159.22 |
| 3,515,656 | 6/1970 | Huang et al. | 204/159.22 |
| 3,615,454 | 10/1971 | Cescon et al. | 204/159.22 |
| 3,725,116 | 4/1973 | Parker et al. | 204/159.22 |
| 3,804,735 | 4/1974 | Radlove et al. | 204/159.22 |
| 3,817,845 | 6/1974 | Feinberg | 204/159.22 |

*Primary Examiner*—Eugene C. Rzucidlo
*Attorney, Agent, or Firm*—Charles A. Huggett; Michael G. Gilman

[57] ABSTRACT

Relatively water insoluble hydroxy functional monoethylenic polyethers or polyesters of monoethylenic carboxylic acids or hydroxy aklys esters thereof are formed by adducting the monoethylenic acid or its hydroxy ester with an anhydride selected from monoepoxides, lactones, or mixtures thereof in the presence of a Lewis acid catalyst, such as $BF_3$ etherate, at a temperature below that at which the unsaturation is consumed, typically about 30°–70° C. These adducts are of low volatility and of low toxicity and can be radiation cured in admixture with polyacrylates to form coatings having improved resistance to elevated temperature exposure.

11 Claims, No Drawings

RADIATION CURABLE COATINGS CONTAINING HYDROXY FUNCTIONAL POLYETHERS AND POLYESTERS OF MONOETHYLENIC ACIDS OR HYDROXY ESTERS THEREOF

This application is a continuation-in-part of my prior application Ser. No. 618,101 filed Sept. 30, 1975, now abandoned.

The present invention relates to relatively water insoluble hydroxy functional polyethers or polyesters of acrylic or similar monoethylenic carboxylic acids, or hydroxy alkyl esters thereof; to the production of such compounds; and to the preparation of polyacrylates and similar polyethylenic compounds therefrom, and to radiation curable coating compositions containing the same.

The reaction of one mole of monoepoxide with one mole of monoethylenic monocarboxylic acid to produce hydroxy functional adducts, such as hydroxyethyl acrylate, is well known, but such compounds tend to be toxic and volatile. It is also known to react a preformed methyl polyoxyethylene structure with acrylic acid or similar compound, as in U.S. Pat. Nos. 3,052,648 and 3,075,031, but these products exhibit extensive solubility in water, and it is desired to minimize water solubility since this leads to water sensitivity in cured coatings containing the same. Additionally, these materials do not contain an hydroxyl group which can then be used to prepare polyethylenic derivatives.

In accordance with this invention, the monoethylenically unsaturated carboxylic acid or hydroxy alkyl derivative thereof is reacted with an appropriate proportion of an anhydride of a dihydric alcohol or an hydroxy acid (a monoepoxide or a lactone) containing at least three carbon atoms. These are particularly illustrated by 1,2-propylene oxide, which is the anhydride of 1,2-propylene diol, or by epsilon-caprolactone, which is the anhydride of the corresponding hydroxy acid. The use of other similar anhydrides will be discussed hereinafter.

In the preferred practice of the invention, an hydroxy alkyl ester of the monoethylenic carboxylic acid is reacted (adducted) with at least about 1 mole of a monoepoxide or lactone containing at least three carbon atoms in the presence of a Lewis acid catalyst, such as $BF_3$ etherate or stannic chloride, and at a typical temperature of about 30°–70° C. Under these conditions, an ether or ester forms, the average number of added groups corresponding to the number of moles of monoepoxide or lactone employed. The unsaturation must be maintained in the product, and this limits the temperature of the reaction which is exothermic. By slow addition of the monoepoxide or lactone, and in the presence of inhibitors, higher temperatures up to about 120° C. may be used, but practical operation suggests an upper limit of about 80° C. Very low temperatures are also useful, but the reaction slows with decreasing temperature. In the same way, the adduction reaction can be carried out with the monoethylenic acid itself, but now one must use at least 2 moles of the monoepoxide or lactone. Moreover, the monoepoxide reactant or the lactone reactant can be constituted by a mixture of monoepoxides or a mixture of lactones, or a mixture of the two.

It is preferred to react at least about 3 moles of the monoepoxide and/or lactone with the monoethylenic carboxylic acid or hydroxy alkyl ester thereof since this maximizes water resistance and ultraviolet sensitivity, and it significantly reduces volatility and toxicity. The polyethers provide the best ultraviolet sensitivity, and are preferred.

There is normally little purpose served by using more than 10 moles of the monoepoxide and/or lactone on the basis noted above, but so long as the reaction is substantially complete or if unreacted monoepoxide or lactone is removed, the product is useful in this invention.

Various monoepoxides may be used herein, such as propylene oxide, butylene oxide, butyl glycidyl ether, phenyl glycidyl ether, cyclohexene oxide, and the like. The oxirane group is preferably carried by an aliphatic group. While other functionality which is inert under the conditions of reaction may be present, such as the halogen group as in epichlorohydrin, it is usually preferred that a single 1,2-epoxide group be the sole functional group present. Propylene oxide is the preferred monoepoxide. While the 1,2-epoxide group is preferred, this is not essential and tetrahydrofuran and 1,3-dioxolane are fully useful to illustrate this. In some instances, and to provide polyacrylates directly, glycidyl acrylate may be used, particularly together with a conventional monoepoxide such as propylene oxide. While ethylene oxide produces undesired water solubility when used alone, it is possible to have some of it present herein where other agents overcome or minimize the problem of water sensitivity.

Various lactones may be used, such as butyrolactone or caprolactone. Epsilon caprolactone is the preferred lactone. The lactone is not reacted with the unsaturated acid in the absence of an epoxide since hydroxy functional derivatives are desired.

The monoethylenic carboxylic acid is preferably acrylic acid, but other similar acids, such as methacrylic acid, and crotonic acid are also useful. The acid is preferably monocarboxylic, but polycarboxylic acids may be used, such as itaconic acid or fumaric acid. Monobutyl maleate and monohydroxypropyl maleate will further illustrate useful monoethylenic carboxylic acid These monoethylenic acids can be used as such, or they can be employed in the form of hydroxy alkyl esters in which the alkyl group preferably contains from 2–4 carbon atoms. These esters are typified by hydroxyethyl acrylate. The monofunctional acids noted before and the hydroxy esters thereof provide monofunctional adducts, and these are best for producing polyethylenic derivatives as by reaction with up to a stoichiometric proportion of organic polyisocyanate, such as toluene diisocyanate, or with a stoichiometric proportion of polycarboxylic acid polyanhydride, such as benzophenone-tetracarboxylic acid dianhydride, or a low molecular weight styrenemaleic anhydride copolymer. Other compounds which contain a plurality of groups capable of adducting with active hydrogen are also useful, such as polyepoxides (Epon 828 is illustrative), and dimethyl dichlorosilane or methyl trichlorosilane.

The selection of benzophenone-tetracarboxylic acid dianhydride is particularly preferred since this leads directly to ultraviolet curable reaction products, especially polyacrylates, which are internally sensitized to ultraviolet light. This permits omission of photosensitizers, such as benzophenone.

The reaction of the adducts of this invention with the organic polyisocyanates or the polycarboxylic acid polyanhydrides or other similar compound is a simple addition reaction which proceeds at moderate temperature (20° C. - 100° C., preferably 50° C. - 80° C.). The unsaturation is not destroyed in this reaction.

It should be observed that the reaction product of 2 moles of hydroxyethyl acrylate and 1 mole of toluene diisocyanate is a solid. Replacing the hydroxyethyl acrylate with the 5 mole propylene oxide adduct thereof produces a liquid diacrylate, and the liquid form is much more attractive, since it can be used without solvents. Also, the final cured products are less brittle.

Ultraviolet curable resins are particularly contemplated, and these, by virtue of the polyether or polyester structure provided herein, and also because of the lowered volatility and reduced toxicity, are easily handled, and cured excellently. Particularly where the polyether structure is present, amine cosensitizers are not needed, and while they will still benefit the cure somewhat, the amines create yellowing or extraction problems, and their omission can be important in certain instances.

The adducts of this invention and the polyethylenic derivatives thereof can be used alone, or they can be combined with other ethylenically unsaturated monomers and polymers to provide radiation curable systems which are particularly useful for coating.

Other ethylenically unsaturated materials which may be present are illustrated by styrene, acrylonitrile, butylene glycol diacrylate, trimethylol propane triacrylate, pentaerythritol triacrylate, epoxy polyacrylates (both di and tetraacrylates) and maleic polyesters.

In connection with the use of other ethylenically unsaturated materials as noted above, it is stressed that the monoethylenic adducts of this invention possess minimal water solubility and significantly reduced volatility and toxicity. However, when these monoethylenic adducts are cured with radiation, the cured products are sensitive to heat and are badly degraded by exposure to heat. This degradation is easily measured by noting the loss of weight which is experienced when the cured materials are subjected to elevated temperature.

As a feature of this invention, it has been found that having the monoethylenic adduct in admixture with a relatively small proportion of a polyacrylate provides radiation cured products possessing greatly enhanced resistance to elevated temperature.

The term "polyacrylate" is a conventional term used to define a compound which provides a plurality of ethylenically unsaturated acrylic acid ester groups. These are provided by esterifying more than one hydroxy group of a polyhydric alcohol with acrylic acid. The reaction may be carried out using direct esterification or transesterification. The polyhydric alcohols may be simple aliphatic polyols illustrated by ethylene glycol, butylene glycol, glycerin, trimethylol propane, pantaerythritol, and the like. Trimethylol propane triacrylate (at least 90% acrylate) or pentaerythritol triacrylate are preferred. It is not necessary to esterify all of the hydroxy groups which are available so long as a plurality of acrylic acid ester groups is provided, preferably at least 2.0 per molecule. While the above polyacrylates are primarily contemplated for admixture with the monoethylenic adducts described herein, these monoethylenic adducts can be used to provide polyacrylates, as described hereinbefore, which are also useful herein to increase resistance to elevated temperature exposure. Solvent soluble resinous polyacrylates are also useful, such as diglycidyl ethers of a bisphenol, such as bisphenol A, having a molecular weight average, by calculation, in the range of about 350 to about 4000, and which have been esterified with acrylic acid or etherified with hydroxy ethyl acrylate, or otherwise reacted to include at least two acrylic groups per molecule.

The polyacrylates are used herein in admixture with the monoethylenic adducts in a weight ratio of polyacrylate to adduct of from 2:98 to 50:50, but the preferred proportions are from 5:95 to 25:75.

It should be particularly noted that the capacity of polyacrylates to greatly improve the resistance to elevated temperature exposure is unusual since polyacrylates do not normally provide this result, as for example when hydroxy ethyl acrylate is radiation cured instead of an adduct thereof.

The invention is illustrated in the examples which follow.

EXAMPLE 1

Charge a dry reaction vessel fitted with a stirrer, thermometer, condenser, drying tube and two additional funnels with 928g hydroxyethyl acrylate (8.0 moles). Add enough borontrifluoride etherate to initiate the reaction, approximately 1 ml. Then, with suitable cooling, add 2320g propylene oxide (40.0 moles) and additional BF$_3$ etherate (15–20 ml.) at such a rate so as to maintain reaction temperature at 50° C. Total addition time is 2–2.5 hours. Maintain the temperature as high as possible by decreasing cooling. When the temperature drops to about 40° C., sample the reaction for gas chromatography. When gas chromatography shows no propylene oxide, add 0.32g hydroquinone (100 parts per million) and 2 ml. triethylamine to stabilize the product. The product is a clear, light yellow liquid of 35–40 centipoise viscosity. A complete gas chromatography analysis indicates the product is a mixture of hydroxyethyl acrylate (~2%) and adducts thereof having the formula shown below in which x ranges from 1 to about 10, and has an average value of 5. NMR analysis of the products shows the correct ratio of vinyl protons to the remaining types of protons and infrared analysis shows the presence of hydroxyl, acrylate unsaturation and ether bands, all consistent with the following structure:

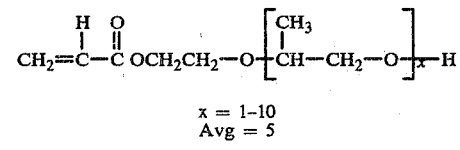

x = 1–10
Avg = 5

EXAMPLE 2

Following the procedure of Example 1, except using 10 moles of propylene oxide to 1 mole of hydroxyethyl acrylate, the product is a light colored liquid of 70–75 centipoise viscosity with the structure noted in Example 1, but with x averaging 10.

EXAMPLE 3

Following the procedure of Example 1, except using 6 moles of propylene oxide to 1 mole of acrylic acid, the product has the structure noted below:

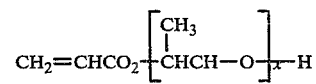

-continued
x = 6 (average)

EXAMPLE 4

Following the procedure of Example 1, except using 3 moles of butylglycidyl ether to 1 mole of hydroxyethyl acrylate yields an adduct having an average of three butylglycidyl ether groups per molecule of hydroxyethyl acrylate.

EXAMPLE 5

Following the procedure of Example 1, except using four moles of propylene oxide and 1 mole of phenyl glycidyl ether to 1 mole of hydroxyethyl acrylate yields an adduct having an average of 4 propylene oxide groups and 1 phenyl glycidyl ether group per molecule of hydroxyethyl acrylate.

EXAMPLE 6

Following the procedure of Example 1, except using 4 moles of propylene oxide and 1 mole of tetrahydrofuran to 1 mole of hydroxyethyl acrylate yields an adduct having an average of 4 propylene oxide groups and 1 tetrahydrofuran group per molecule of hydroxyethyl acrylate.

EXAMPLE 7

Following the procedure of Example 1, except using 4 moles of propylene oxide and 1 mole of epsilon-caprolactone to 1 mole of hydroxyethyl acrylate yields an adduct having an average of 4 propylene oxide groups and 1 caprolactone group per molecule of hydroxyethyl acrylate.

EXAMPLE 8

To 406 grams of the hydroxyethyl acrylate-propylene oxide adduct produced in Example 1 are added 28.7 grams of the commercial 80/20 isomeric mixture of toluene diisocyanates, 0.17 gram hydroquinone and 3 drops dibutyl tin dilaurate cataylst. The reaction mixture is heated at 60°-65° C. for about 2 hours after which the infrared spectrum shows complete reaction of the isocyanate. The product is a low viscosity liquid [(Gardner-Holdt =G, (165 centipoise)] containing a mixture of a diacrylate resin and unreacted monoacrylate monomer. The structure of the diacrylate resin is shown below:

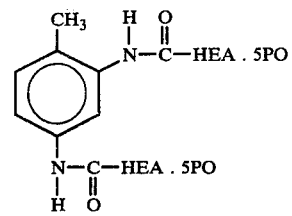

HEA identifies hydroxyethyl acrylate
PO identifies propylene oxide.

EXAMPLE 9

To 406 grams of the hydroxyethyl acrylate-propylene oxide addition product of Example 1 are added 40.3 grams benzophenonetetracarboxylic dianhydride, 2.2 grams triethyl amine, and 0.178 grams hydroquinone. The reaction mixture is heated at 70° C. for 3-4 hours after which the infrared spectrum shows no anhydride remaining. At this point the reaction mixture consists of a difunctional acrylate resin and a monofunctional acrylate monomer of low viscosity [(Gardner-Holdt = J (250 centipoise)]. The structure of the diacrylate is shown below:

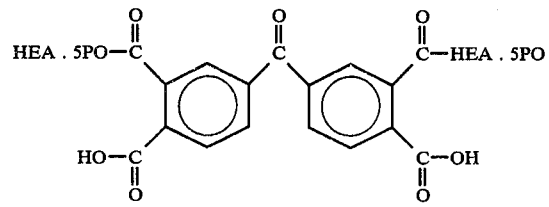

HEA identifies hydroxyethyl acrylate
PO identifies propylene oxide.

The benzophenonetetracarboxylic dianhydride, as will be shown hereinafter, provides photosensitive characteristics, rendering the product intrinsically sensitive to ultraviolet light in the absence of any additional photosensitizer.

EXAMPLE 10

Simple coating formulations based on the products described in the previous examples, pentaerythritol triacrylate and a photosensitizer, were drawn down on metal panels using a #3 wire wound rod. The coatings were cured by exposure to 2 × 200 watt/inch medium pressure mercury lamps at a speed of 25 feet per minute in air. The compositions and surface characteristics of the coatings are shown in Table I which also shows how much of the film remains after baking 5 minutes at 350° F.

Table I

| Pentaerythritol Triacrylate % | Hydroxypolyoxyalkylene Acrylate | | Sensitizer (note 1) | Surface Tack | Film Yield % |
| --- | --- | --- | --- | --- | --- |
| 30 | HEA . 5PO | 63% | 7% | Tack Free | 85 |
| 28 | HEA . 4PO.1Cl | 65% | 7% | Tack Free | 77 |
| 27 | HEA . 4PO.1PGE | 66% | 7% | Tack Free | 88 |
| 26 | HEA . 3BGE | 67% | 7% | Slight Tack | 82 |

Table I-continued

| Pentaerythritol Triacrylate % | Hydroxypolyoxyalkylene Acrylate % | | Sensitizer (note 1) | Surface Tack | Film Yield % |
|---|---|---|---|---|---|
| 30 | HEA . 4PO.1THF | 63% | 7% | Tack Free | 85 |

Note 1
The sensitizer is a weight ratio mixture of 5 parts benzophenone to 2 parts methyldiethanol amine
HEA identified hydroxyethyl acrylate
PO identified propylene oxide
PGE identifies phenyl glycidyl ether
Cl identifies caprolactone(epsilon)
BGE identifies butyl glycidyl ether
THF identifies tetrahydrofuran

EXAMPLE 11

This example describes a unique advantage when using the products of this invention. For example, in Table I above, the sensitizer is shown to be a combination of benzophenone (5 parts) and methyldiethanol amine (2 parts). It is also possible to use benzophenone alone without the methyldiethanol amine cosensitizer. A formulation identical to that in Table I with HEA.4-PO.1PGE without methyldiethanol amine cured to a yield of 87% vs. 88% with methyldiethanol amine present. Thus, the products of this invention surprisingly cure well in the absence of amine sensitizers which are usually needed for a good ultraviolet cure in an air atmosphere.

EXAMPLE 12

In the previous example, the products of this invention were used without resins, but it is also possible to use these in admixture with other resinous materials, including other radiation curable materials. The formulating latitudes available are illustrated in Table II below. These materials were applied and cured under the conditions set forth in Example 10.

Table II

| Polymer Type % | Trimethylol Propane Triacrylate % | HEA . 5PD % | Sensitizer Note 1 of Table I | Surface Tack | Yield % |
|---|---|---|---|---|---|
| A-Urethane 21% | 21% | 51% | 7% | Slight | 89 |
| B-Urethane 21% | 21% | 51% | 7% | Tacky | 87 |
| C-Urethane 21% | 21% | 51% | 7% | Slight | 88 |
| D-Urethane 21% | 21% | 51% | 7% | Slight | 90 |
| E-Epoxyacrylate 23% | 21% | 49% | 7% | Tack Free | 88 |

A = Polycaprolactone Diol-Toluene Diisocyanate-Diacrylate
B = Dimer Acid Diisocyanate-Diacrylate
C = Polyether Diol-Toluene Diisocyanate-Diacrylate
D = Isophoronediisocyanate-Diacrylate
E = Epon 828-Diacrylate

EXAMPLE 13

To the composition of Example 8 (30 grams) was added 5.3 grams trimethylolpropane triacrylate, 1.8 gram benzophenone and 0.74 gram methyldiethanol amine. The coating was drawn down on aluminum panels with #3 wire wound rod and cured by passing the coated panel at 25 feet per minute under 2 × 200 watt/inch medium pressure mercury lamps. The coating cured to a hard, tack free, mar resistant surface with a yield of 90+% after baking 5 minutes at 350° F.

EXAMPLE 14

To the composition of Example 9 (30 grams) was added 5.3 grams trimethylolpropane triacrylate, 1.8 gram benzophenone, and 0.74 gram methyldiethanol amine. The coating was cured as in Example 13 above.

The coating cured to a hard, tack free, mar resistant surface, with an after-bake yield of 77%.

EXAMPLE 15

To the composition of Example 9 (20 grams) was added 6.7 grams pentaerythritol triacrylate. The coating was cured as in Example 13 above. The coating cured to a tack free, mar resistant surface with an after-bake yield of 76%. This example illustrates a unique property, namely, that a photosenzitizer can be incorporated into the resin component, thereby rendering it completely reactive. That is, it cannot be extracted from the cured composition because it is an integral part of this coating

EXAMPLE 16

Following the procedure of Example 1, except using 4 moles of propylene oxide and 1 mole of glycidyl acrylate to 1 mole of acrylic acid, the product was a liquid containing an average of 4 propylene ether groups and 1

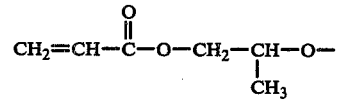

group per molecule, providing a liquid polyacrylate in a quick and convenient manner. This product cures in the same manner as the product of Example 1, but ultraviolet cure superiority can be expected to flow out of the presence of the second acrylate moiety.

The function of a small proportion of polyacrylate in the radiation curable coating compositions of this invention is particularly illustrated in the following examples which demonstrate the enormous improvement in thermal stability which is obtained.

In each instance in the following comparison, a liquid coating composition containing 5 weight percent of a photosensitizer mixture (a 3:2 weight ratio mixture of benzophenone and methyl diethanol amine) was drawn down on metal panels (aluminum) using a #3 wire wound rod and the coatings were cured in air by exposure to 2 × 200 watt/inch mercury lamps at a speed of 25 feet per minute. The results are tabulated as follows:

| Coating Composition | Film Yield %* | Extracted** |
|---|---|---|
| HEA . 5PO/photosensitizer 95/5 | 40 | 90 |
| HEA . 5PO/PETA/photosensitizer 85/10/5 | 80 | 95 |
| HEA . 5PO/PETA/photosensitizer 65/30/5 | 85 | 95 |

*using a post bake of 5 minutes at 350° F.
**These films were thicker (1 mil) and lubricated steel panels were used to facilitate stripping of the film. The solvent used was methyl ethyl ketone and the films were immersed overnight.

PETA is pentaerythritol triacrylate.

As can be seen, the presence of a minor proportion of polyacrylate provided only a small increase in solvent resistance, thus establishing that the radiation cure for all the films was a reasonably complete cure. The thermal stability, on the other hand, was totally changed. The adduct by itself degraded rapidly, 60% of the material being removed by only a 5 minute bake at 350° F. Only 10% of polyacrylate improved this so greatly that only 20% of the material was removed after the bake, and 30% of polyacrylate provided further improvement so that the system only lost 15% of its film weight after the bake.

As will be seen, a relatively small proportion of polyacrylate provides a vast improvement in the thermal stability of the radiation cured material.

The invention is defined in the claims which follow.

I claim:

1. A radiation curable coating composition comprising a monoethylenic adduct of a monoethylenic carboxylic acid or hydroxy alkyl ester thereof with an anhydride containing at least 3 carbon atoms and selected from the group consisting of monoepoxides, lactones, and mixtures thereof, said adduct containing an average of at least 1 mole of said anhydride per mole of said hydroxy ester or an average of at least 2 moles of said anhydride per mole of said acid, said monoethylenic adduct being in admixture with a polyacrylate providing a plurality of ethylenically unsaturated acrylic acid ester groups.

2. A radiation curable coating composition as recited in claim 1 in which said composition includes a photosensitizer rendering the composition curable with ultraviolet light.

3. An ultraviolet curable coating composition as recited in claim 2 in which said composition is free of amine cosensitizer.

4. An ultraviolet curable coating composition as recited in claim 4 in which said adduct contains an average of from about 3 to about 10 moles of said anhydride per mole of said acid or hydroxy alkyl ester thereof.

5. An ultraviolet curable coating composition as recited in claim 4 in which said anhydride is selected from the group consisting of propylene oxide, butylene oxide, butyl glycidyl ether, cyclohexane oxide, phenyl glycidyl ether, tetrahydrofuran, and epsilon caprolactone, and said monoethylenic carboxylic acid is acrylic acid.

6. An ultraviolet curable coating composition comprising a monoethylenic adduct of acrylic acid or hydroxy alkyl ester thereof with an anhydride containing at least three carbon atoms and selected from the group consisting of monoepoxides and mixtures thereof with lactones, said adduct containing an average of from 3 to about 10 moles of said anhydride per mole of said acid or alkyl ester thereof and said anhydride comprising propylene oxide, said monoethylenic adduct being in admixture with a polyacrylate providing a plurality of ethylenically unsaturated acrylic acid ester groups, said composition further including a photosensitizer rendering the composition sensitive to ultraviolet light.

7. An ultraviolet curable coating composition as recited in claim 6 in which said composition is free of amine cosensitizer.

8. An ultraviolet curable coating composition as recited in claim 7 in which said polyacrylate contains at least 2.0 acrylic acid ester groups per molecule.

9. An ultraviolet curable coating composition as recited in claim 6 in which said monoethylenic adduct is present in a weight ratio of polyacrylate to monoethylenic adduct of from 2:98 to 50:50.

10. An ultraviolet curable coating composition as recited in claim 8 in which said monoethylenic adduct is present in a weight ratio of polyacrylate to monoethylenic adduct of from 5:95 to 25:75.

11. An ultraviolet curable coating composition as recited in claim 10 in which said polyacrylate consists essentially of trimethylol propane triacrylate.

* * * * *

UNITED STATES PATENT AND TRADEMARK OFFICE
CERTIFICATE OF CORRECTION

PATENT NO. : 4,126,527
DATED : November 21, 1978
INVENTOR(S) : Marvin L. Kaufman It is certified that error appears in the above-identified patent and that said Letters Patent are hereby corrected as shown below:

Columns 7 and 8, in the heading for Table II "HEA.5PD" should read --HEA.5PO--.

Column 10, line 9 numeral "4" should read --1--.

Signed and Sealed this

Tenth Day of April 1979

[SEAL]

Attest:

RUTH C. MASON
Attesting Officer

DONALD W. BANNER
Commissioner of Patents and Trademarks